(12) United States Patent
Schroder et al.

(10) Patent No.: US 6,936,260 B1
(45) Date of Patent: Aug. 30, 2005

(54) VACCINE COMPOSITION

(75) Inventors: Ulf Schroder, Sundbyberg (SE); Stefan Svenson, Enskede (SE)

(73) Assignee: Eurocine AB, Stockholm (SE)

( * ) Notice: Subject to any disclaimer, the term of this patent is extended or adjusted under 35 U.S.C. 154(b) by 0 days.

(21) Appl. No.: 09/926,001

(22) PCT Filed: Feb. 9, 2000

(86) PCT No.: PCT/EP00/01046

§ 371 (c)(1),
(2), (4) Date: Sep. 17, 2001

(87) PCT Pub. No.: WO00/47225

PCT Pub. Date: Aug. 11, 2000

(30) Foreign Application Priority Data

Feb. 12, 1999 (SE) ..................... 9900495

(51) Int. Cl.[7] ........................ A61K 39/04; A61K 39/00; G01N 33/53
(52) U.S. Cl. ................ 424/248.1; 424/184.1; 424/283.1; 424/435; 424/7.1; 424/7.2
(58) Field of Search ............ 424/248.1, 184.1, 424/283.1; 435/7.1, 7.32

(56) References Cited

U.S. PATENT DOCUMENTS 6,451,325 B1 * 9/2002 Van Nest et al.

FOREIGN PATENT DOCUMENTS

| WO | WO 93/06921 | * | 4/1993 |
| WO | WO 9306921 A1 | | 4/1993 |
| WO | WO 94/17827 | * | 8/1994 |
| WO | WO 9417827 A1 | | 8/1994 |
| WO | WO 97/35616 | * | 11/1997 |
| WO | WO 97/47320 | * | 12/1997 |
| WO | WO97/47320 | * | 12/1997 |
| WO | WO 9747320 A1 | | 12/1997 |

OTHER PUBLICATIONS

Youmans et al, Journal of Bacteriology, Jan. 1969, p. 107-113.*
Youmans et al, Journal of Bacteriology, Jan. 1969, p. 103-113.*

* cited by examiner

Primary Examiner—James O. Wilson
Assistant Examiner—Vanessa L. Ford
(74) Attorney, Agent, or Firm—Bacon & Thomas

(57) ABSTRACT

A tuberculosis (TB) vaccine composition is disclosed. The composition comprises, as adjuvant, one or more substances selected from a) monoglyceride preparations having at least 80% monoglyceride content and b) fatty acids of the general formula $CH_3$—$(CH_2)_n$—COOH where "n" may be varied between 4 and 22, and where the acyl chain may contain one or more unsaturated bonds, and as immunizing component, inactivated, e.g. heat killed or formalin killed, *Mycobacterium tuberculosis* bacteria.

36 Claims, 2 Drawing Sheets

VACCINE COMPOSITION

This application claims priority of 371 of PCT/EP00/01046, filed Feb. 9, 2000.

The present invention relates to a novel tuberculosis (TB) vaccine composition. The preferred route of administration is via the mucosal membranes.

BACKGROUND

The earliest described immunization attempts were carried out in China over 900 years ago, where intranasal inoculation of dried and ground smallpox pustules was performed. In the classical immunology and in combination with vaccination against different types of infectious agents e.g. bacteria, virus or parasites the prevailing dogma has been to administer the vaccine subcutaneously or intramuscularly. However, research has during the last years shown that the body has a very effective immunological system that resides in the mucosa. It has also been shown that you can administer vaccines nasally, orally, rectally and vaginally. In the same way as for the classical immunization it has been shown that by mucosal vaccination there is also a need for enhancement of the immunological response by the addition of adjuvants.

The intranasal route has attracted increased attention because of the greater efficacy in inducing mucosal immune responses than the more conventional regimes of parenteral immunization. Furthermore, the realization that approximately 80% of the immune system reside in the mucosa combined with the fact that an equal percentage of the known pathogens enter our bodies via the mucosal membranes has pushed the interest towards the application of mucosal immunization.

It has also been shown that parenteral vaccines do not induce immune response at mucosal sites. Thus, it is also clear that appropriate stimulation of a mucosal site such as the nose or the gut, can generate immune response at other mucosal sites. As an example, it is possible to apply a vaccine in the nose and obtain an immune response in the vagina. Furthermore, the mucosal immune response is very rapid with onset only hours after being subjected to stimulation by a pathogen, as compared to parenteral immunity having a response time of several days.

Tuberculosis (TB) is one of the major causes of morbidity in the world with an estimated death toll of approximately 3 millions per year. It is estimated that ⅓ of the world's population is infected with TB. To a large extent TB is essentially an uncontrolled problem despite the use of the Bacille Calmette-Guérin (BCG) vaccine for more than 75 years.

The BCG vaccine consists of a weakened strain of tuberculosis bacteria taken from a cow in 1908. The original bacteria used today were cultured for 13 years for the purpose of weaken their pathogenic characteristics in order to be used as live bacteria for parenteral vaccination of humans. Basically the same strain is used today as the only vaccine available against TB. Several pharmaceutical companies around the world produce the BCG vaccine. The BCG formulation used today consists of freeze-dried attenuated viable BCG vaccine in one container and another container with physiologically acceptable suspension media. Before administration, the freeze-dried BCG is suspended and subsequently administered by injection to the patient. This procedure which has to be carried out immediately in connection with the vaccination, requires skilled personnel and decent facilities in order to avoid contamination. Unfortunately these criteria are hard to keep up with in the developing countries. Thus, it is estimated that failure to keep to this standard costs about USD 500 millions each year world wide. Consequently, huge savings could be made both in money and product safety, if a system was available where no mixing of vaccines was needed and where injections could be eliminated, thus eliminating the need for highly skilled personnel and sterile conditions.

In clinical trails around the world, the protective efficacy of the BCG vaccine has been shown to vary between −50% to +80%. This means that certain clinical studies have shown that in fact you enhance instead of diminish your risk of getting the disease after vaccination.

The BCG vaccine works well for children but has more or less no effect on adults. Consequently there are great efforts made in order to achieve a vaccine against TB for the grown-up population. Up to date however, there are no reports in the literature of a TB vaccine that is better than BCG.

Tuberculosis is spread by close person-to-person contact through infectious aerosols. On rare occasions the disease can be acquired by ingestion or skin trauma. This means that the first organ to get into contact with the bacteria during a normal infection is the mucosal surfaces in the lungs.

Adjuvants are a heterogeneous group of substances that enhance the immunological response against an antigen that is administered simultaneously.

Almost all adjuvants used today for enhancement of the immune response against antigens are particles or are forming particles together with the antigen. In the book "Vaccine Design—the subunit and adjuvant approach" (Ed: Powell & Newman, Plenum Press, 1995) almost all known adjuvants are described both regarding their immunological activity and regarding their chemical characteristics. As described in the book more than 80% of the adjuvants tested today are particles or polymers that together with the antigens (in most cases proteins) are forming particles. The type of adjuvants that are not forming particles are a group of substances that are acting as immunological signal substances and that under normal conditions consist of the substances that are formed by the immune system as a consequence of the immunological activation after administration of particulate adjuvant systems.

Using particulate systems as adjuvants, the antigens are associated or mixed with or to a matrix, which has the characteristics of being slowly biodegradable. Of great importance using such matrix systems are that the matrices do not form toxic metabolites. Choosing from this point of view, the main kinds of matrices that can be used are mainly substances originating from a body. With this background there are only a few systems available that fulfill these demands: lactic acid polymers, poly-amino acids (proteins), carbohydrates, lipids and biocompatible polymers with low toxicity. Combinations of these groups of substances originating from a body or combinations of substances originating from a body and biocompatible polymers can also be used. Lipids are the preferred substances since they display structures that make them biodegradable as well as the fact that they are the most important part in all biological membranes.

Lipids are characterized as polar or non-polar. The lipids that are of most importance in the present invention are the polar lipids since they have the capacity to interact and form particulate systems in water. Another way of defining these lipids are as amphiphilic due to their chemical structure with one hydrophobic and one hydrophilic part in the molecule thereby being useable as surface active substances.

Examples of main groups of polar lipids are mono-glycerides, fatty acids, phospholipids and glycosphingolipids. These main groups can be further characterized depending on the length of the acyl chain and the degree of saturation of the acyl chain. Since the number of carbon atoms in the acyl chain can be in the range of 6 to 24, and the number of unsaturated bonds can be varied, there is an almost infinite number of combinations regarding the chemical composition of the lipid.

Particulate lipid systems can be further divided into the different groups as discussed in the scientific literature such as liposomes, emulsions, cubosomes, cochleates, micelles and the like.

In a number of systems the lipids may spontaneously form, or can be forced to form, stabile systems. However, under certain circumstances other surface-active substances have to be introduced in order to achieve stability. Such surface-active systems can be of non-lipid character but possess the characteristics of the polar lipids having hydrophobic and hydrophilic parts in their molecular structure.

Another factor that has been shown to be of importance is that lipids exhibit different physical chemical phases, these phases have in different test systems been shown to enhance uptake of biological substances after administration to mucous membranes. Examples of such physical chemical phases described are L2, lamellar, hexagonal, cubic and L3.

In the same way as within the classical immunology where vaccines (antigens) are administered parenterally, there is within mucosal immunization a great interest in directing the immunological response towards development of humoral and/or cellular response. If you obtain a humoral response it would be important to direct the response in a way that a certain class of antibodies would be obtained. In order to obtain such a goal, specific immune stimulating agents can be added to the formulation of antigens and adjuvants.

A formulation which fulfils these goals is described in PCT/SE97/01003, the contents of which is incorporated herein by reference. The disclosed formulation comprises monoglycerides and fatty acids. The monoglycerides comprise one or more substances selected from monoglycerides wherein the acyl group contains from 6 to 24 carbon atoms, preferably 8 to 20 carbon atoms, even more preferably 14-20 carbon atoms and where the acyl chain may contain unsaturated bonds.

The acyl chain of the fatty acid may be varied between 4 and 22, preferably 8 to 18 and where the acyl chain may contain one or more unsaturated bonds. A combination of the monoglyceride mono-olein and oleic acid has shown to be an L3 phase, which can be described as sponge-like structure, in contrast to liposomes that form onion-like lamellar structures.

Said combination of monoglycerides and fatty acids my be further formulated by the addition of a biocompatible and biodegradable oil thus forming an oil in water (o/w) or w/o/w emulsion. Such emulsions have been shown in the literature to be very effective in enhancing the cellular response against an antigen after administration to an animal (Singh, M., et al 1997, Vaccine 15, 1773–78). It is generally accepted that in order to have an acceptable vaccine against TB there is a need for a cellular immune response.

DESCRIPTION OF THE INVENTION

The present invention is directed to a tuberculosis (TB) vaccine composition comprising, as adjuvant, one or more substances selected from
a) monoglyceride preparations having at least 80% monoglyceride content and having the general formula $$\begin{array}{ccc} CH_2 - CH - CH_2 \\ | & | & | \\ O & O & O \\ | & | & | \\ R_1 & R_2 & R_3 \end{array}$$

wherein $R_1$ and $R_2$ is H and $R_3$ is one acyl group containing from 6 to 24 carbon atoms, and where the acyl chains may contain one or more unsaturated bonds and
b) fatty acids of the general formula $CH_3-(CH_2)_n-COOH$ where "n" may be varied between 4 and 22, and where the acyl chain may contain one or more unsaturated bonds, and as immunizing component, inactivated *Mycobacterium tuberculosis* bacteria.

In a preferred embodiment the *M. tuberculosis* bacteria are heat killed or formalin killed.

The adjuvant of the vaccine composition of the invention preferably has a monoglyceride preparation content of at least 90%, preferably at least 95%, and the acyl chains of the monoglyceride preparation contains 8 to 20 carbon atoms, preferably 14 to 20 carbon atoms, and the acyl chains optionally contains one or more unsaturated bonds.

The TB vaccine composition according to the invention may further comprise pharmaceutical excipients selected from the group consisting of biocompatible oils, such as rape seed oil, sunflower oil, peanut oil, cotton seed oil, jojoba oil, squalan or squalene, physiological saline solution, preservatives and osmotic pressure controlling agents, carrier gases, pH-controlling agents, organic solvents, hydrophobic agents, enzyme inhibitors, water absorbing polymers, surfactants, absorption promoters, and anti-oxidative agents.

In a most preferred embodiment of the invention the TB vaccine composition comprises, as adjuvant, a mixture of mono-olein and oleic acid, and possibly soybean oil, and, as immunizing component, heat-killed *M tuberculosis* bacteria.

In a preferred embodiment the TB vaccine composition of the invention is formulated into a preparation for mucosal administration, such as nasal, pulmonary, oral or vaginal administration.

Another aspect of the invention is directed to an aerosol or spray package comprising a TB vaccine composition according to the invention.

A further aspect of the invention is directed to a nose-drop package comprising a TB vaccine composition according to the invention.

Yet another aspect of the invention is directed to method of vaccinating a mammal against Tuberculosis (TB) which comprises mucosal administration to the mammal of a protection-inducing amount of a TB vaccine composition according to the invention.

As described above the present commercially available vaccine against TB comprises of an attenuated strain of the bacteria. Such systems may under certain circumstances, when administered as a vaccine, result in an infection by the attenuated bacteria. Thus, attenuated systems are preferentially used when killed organisms are unable to give protective immunity. Thus, the preferred system is an inactivated organism or a purified antigen from the pathogen, which, in combination with adequate adjuvants results in protective immunity. Furthermore, inactivated pathogens are more stable and consequently more attractive as antigens/vaccines, especially in the developing world. Such inactivation may be performed by heat or by treatment with formalin, both of which is well established and well known to the man skilled in the art.

The TB vaccine composition according to the invention may be prefabricated, and no need for skilled personnel is needed upon nasal administration, thereby eliminating injection systems such as needles and syringes which in developing world often are contaminated and thus are spreading diseases between patients. Furthermore, a device for multi-dose aerosol delivery of a nasal vaccine can easily be constructed in way that no person-to-person infection can occur.

The invention will now be illustrated by way of an example, which, however, is not to be interpreted as limitation to the scope of protection according to the appended claims.

SHORT DESCRIPTION OF THE DRAWINGS

EXAMPLE 1

BCG

Protection of C57BL mice from intranasal sub-lethal challenge with *M. tuberculosis* (MT) by immunization with live BCG and heat-killed BCG in two different L3 lipid adjuvant formulations.

Emulsion; one ampoule of freeze-dried BCG bacteria was suspended in the suspension media as supplied by the manufacturer (Statens Seruminstitute, Denmark) and heat-killed at +60° C. for 10 minutes. The emulsion was produced by mixing the heat-killed BCG suspension with 200 µl of soybean oil and 110 µl of a mixture of mono-olein and oleic acid (1:1). This mixture was sonicated briefly for a few seconds whereupon 3.2 ml of 0.1 M TRIS buffer and 40 µl of 4 M NaOH were added. Sonication was performed for 2 minutes whereupon the emulsion was used for immunization.

An L3 suspension is produced from a 1:1 molar mixture of mono-olein and oleic acid (1.43 g of mono-olein and 1.12 g of oleic acid) which was added to 20 ml of 0.1 M Triss buffer. Prior to sonication for 2 minutes, 640 µl of 4 M NaOH are added. Before immunization the L3 adjuvant is mixed at a 1:1 ratio with the heat-killed BCG.

Adjustments of the amount of suspension media were made so that each mouse received the same amount of BCG bacteria whether given parenterally or nasally.

Immunization 1; 0 weeks (parenteral for all groups). Immunization 2; 3 weeks (nasally for all groups except live BCG which was administered parenterally). Challenge; 4 weeks.

Changes of body weight (%) related to initial weight at time 0 weeks.

Figure 1:
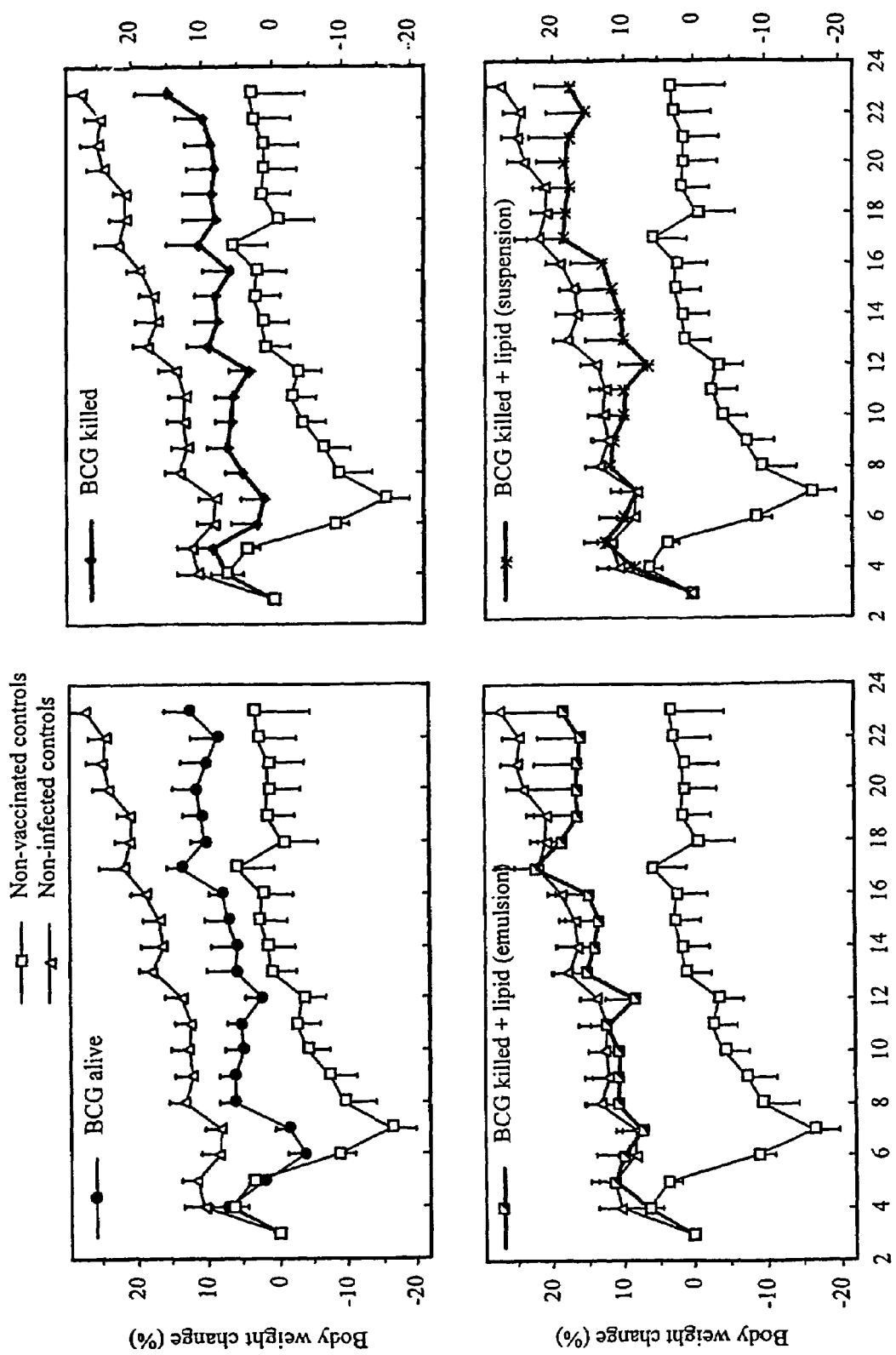
FIG. 1 shows the results of the testing disclosed in Example 1.

Average body weight changes±SE are shown in FIG. 1.

As can be seen from the weight changes both of the adjuvant formulations containing heat-killed BCG result in a positive body-weight development as compared to non-adjuvanted BCG (alive or killed).

Figure 2:
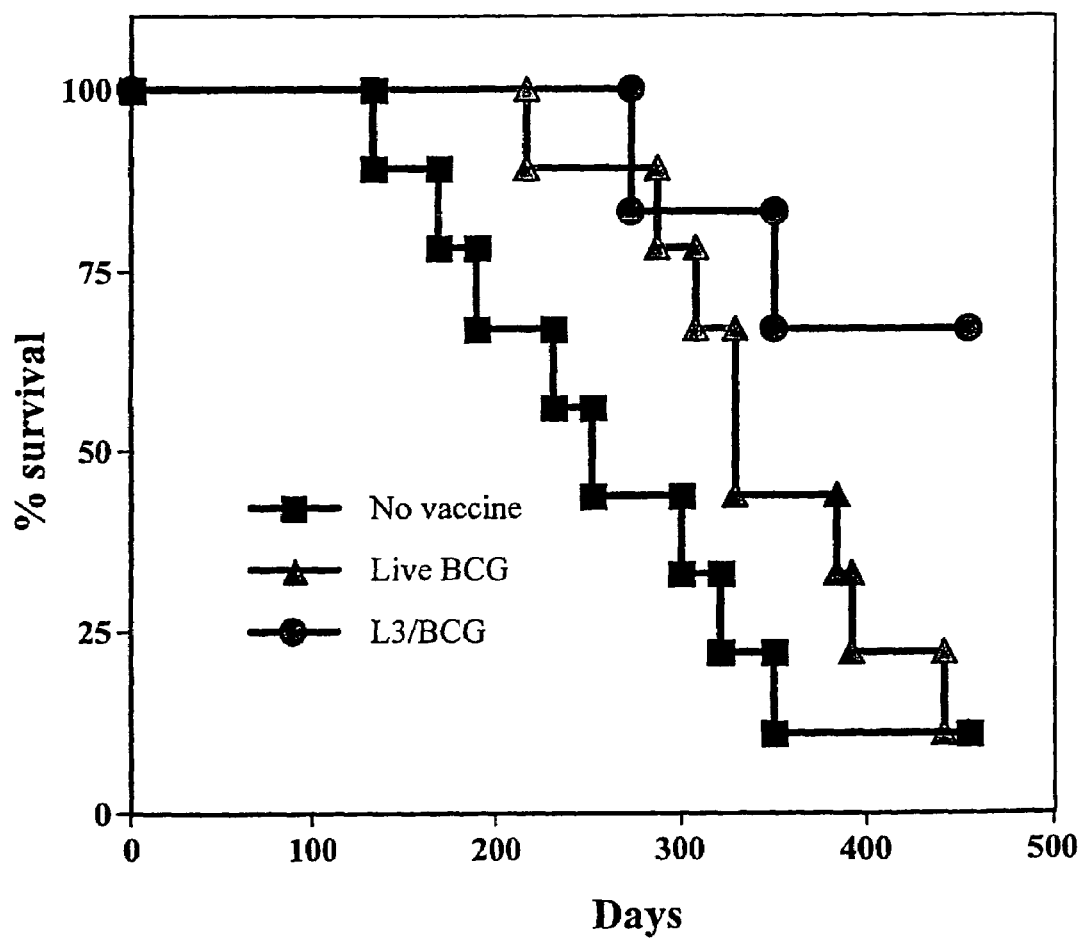
FIG. 2 shows the survival rate for the same mice as described in FIG. 1.

In FIG. 2 is seen the survival rate for the same mice as described in FIG. 1. As can be seen approximately 70% of the mice receiving heat-killed BCG formulated with the lipid adjuvant according to the present invention were still alive when the experiment was terminated. In contrast, in the groups receiving classical live BCG or no vaccine at all, only approximately 10 of the mice were alive when the experiment was terminated.

EXAMPLE 2

Mice (female) were immunised on day 0 and after 3 weeks with different vaccine formulations whereupon the mice were killed after 11 weeks. The spleens of the mice were taken out and the lymphocytes were purified and subsequently subjected to immunological assays in order to establish the efficacy of the formulations to induce immunologically active lymphocytes.

In the following example, the lymphocytes were stimulated with an extract from *M. tuberculosis*. Simultaneously $^3$H-labelled thymidine was added to the cells. As the immunologically activated cells proliferate, the $^3$H-labelled thymidine is incorporated into the genomes of the proliferating cells. Next, the $^3$H-labelled thymidine was measured. A high uptake of labelled thymidine indicates the strength of the lymphocyte immune response.

The following vaccine formulations were tested:

BCG: Live standard BCG vaccine (Statens Seruminstitute, Denmark) injected into three mice on day 0.

BCG/L3: Live standard BCG vaccine (Statens Seruminstitute, Denmark) was used as primary vaccination and subsequently the mice were vaccinated intra-nasally with a heat-killed BCG/L3 vaccine, (according to Example 1) as a booster-vaccination on day 21.

L3/L3: On day 0 the mice were injected with the heat-killed BCG/L3 formulation according to Example 1, followed by a nasally administered booster vaccination after 3 weeks using the same formulation.

The results are presented in Table 1.

TABLE 1

| Formulation | $^3$H-thymidine uptake (cpm) |
| --- | --- |
| BCG | 2153 |
| BCG/L3 | 1337 |
| L3/L3 | 4583 |

The results indicate that the formulation according to the present invention is superior in stimulating lymphocytes as compared to standard BCG vaccination with live BCG.

EXAMPLE 3

Another set of mice was subjected to the same vaccination procedures and formulations as described in Example 2 above. However, 8 weeks after the booster immunization the mice were challenged with a *M. tuberculosis*-containing aerosol. Another 4 weeks later the mice were killed and the lymphocytes from the spleens were collected. The lymphocytes were allowed to grow for five days whereupon the amounts of Tumor Necrosis Factor Alfa (TNF-α) were determined in cell-supernatants. Elicitation of low levels of TNF-α is a desired property of any new vaccine candidate against tuberculosis because of its well-documented noxious side effects and hence, any candidate vaccine that can prevent TNF-α production upon infection would be regarded as superior.

Table 2. Concentrations of TNF-α as compared to a group of mice that has been challenged on week 11 with *M tuberculosis* without prior immunization.

TABLE 2

| Formulation | TNF-α (pg) |
|---|---|
| BCG | 43 |
| BCG/L3 | 18 |
| L3/L3 | 9 |
| Challenge only | 60 |

As can be seen from Table 2, the present invention using heat killed BCG together with an emulsion according to the present invention results in the lowest level of TNF-α.

What is claimed is:

1. A Tuberculosis (TB) vaccine composition comprising an adjuvant comprising one or more substances selected from the group consisting of:
a) monoglyceride preparations having at least 80% monoglyceride content and having a formula:

$$\begin{array}{ccc} CH_2 - CH - CH_2 \\ | & | & | \\ O & O & O \\ | & | & | \\ R & R & R \end{array}$$

wherein R is H or an acyl group containing from 6 to 24 carbon atoms with the proviso that two of the R groups are H and b) a fatty acid with 6 to 24 carbon atoms and as immunizing component, inactivated *Mycobacterium tuberculosis* bacteria.

2. The TB vaccine according to claim 1, wherein the *M. tuberculosis* bacteria are heat or formalin killed.

3. The TB vaccine composition according to claim 1, wherein the adjuvant has a content of monoglyceride in the monoglyceride preparation of at least 90%, and the acyl chains of the monoglyceride in the monoglyceride preparation contains 8 to 20 carbon atoms.

4. The TB vaccine composition according to claim 1, wherein the adjuvant has a content of monoglyceride in the monoglyceride preparation of at least 95% and the acyl chains of the monoglyceride in the monoglyceride preparation contains 14 to 20 carbon atoms.

5. The TB vaccine composition according to claim 1, which further comprises pharmaceutical excipients selected from the group consisting of biocompatible oils, physiological saline solutions, preservatives, osmotic pressure controlling agents, carrier gases, pH-controlling agents, organic solvents, hydrophobic agents, enzyme inhibitors, water absorbing polymers, surfactants, absorption promoters and anti-oxidative agents.

6. The TB vaccine composition according to claim 1, wherein the monoglyceride preparation is mono-olein and the fatty acid is oleic acid, the immunizing component is heat-killed *M. tuberculosis* bacteria.

7. The TB vaccine composition according to claim 5, wherein the adjuvant further comprises soybean oil.

8. The TB vaccine composition according to claim 1, wherein the composition is formulated into a preparation for mucosal administration.

9. The TB vaccine composition according to claim 8, wherein the mucosal administration is nasal, pulmonary, oral or vaginal administration.

10. An aerosol or spray package comprising a TB vaccine composition comprising an adjuvant comprising one or more substances selected from the group consisting of: a) monoglyceride preparations having at least 80% monoglyceride content and having the formula:

$$\begin{array}{ccc} CH_2 - CH - CH_2 \\ | & | & | \\ O & O & O \\ | & | & | \\ R & R & R \end{array}$$

wherein R is H or an acyl group containing from 6 to 24 carbon atoms with the proviso that two of the R groups are H, and b) a fatty acid with 6 to 24 carbon atoms, and as immunizing component, inactivated *Mycobacterium tuberculosis* bacteria.

11. An aerosol or spray package according to claim 10, ein the *M. tuberculosis* bacteria are heat or formalin killed.

12. An aerosol or spray package according to claim 10, wherein the adjuvant has a content of monoglyceride in the monoglyceride preparation of at least 90%, acyl chains of the monoglyceride in the monoglyceride preparation and contains 8 to 20 carbon atoms.

13. An aerosol or spray package according to claim 10, wherein the adjuvant has a content of monoglyceride in the monoglyceride preparation of at least 95% and the acyl chains of the monoglyceride preparation contains 14 to 20 carbon atoms.

14. An aerosol or spray package according to claim 10, which further comprises pharmaceutical excipients selected from the group consisting of biocompatible oils, physiological saline solutions, preservatives, osmotic pressure controlling agents, carrier oases, pH-controlling agents, organic solvents, hydrophobic agents, enzyme inhibitors, water absorbing polymers, surfactants, absorption promoters and anti-oxidative agents.

15. An aerosol or spray package according to claim 10, wherein the monoglyceride preparation is mono-olein and the fatty acid is oleic acid, and the immunizing component is heat-killed *M. tuberculosis* bacteria.

16. An aerosol or spray package according to claim 10, wherein the composition is formulated into a preparation for mucosal administration.

17. An aerosol or spray package according to claim 16, wherein the mucosal administration is nasal, pulmonary, oral or vaginal administration.

18. An aerosol or spray package according to claim 15, wherein the adjuvant further comprises soybean oil.

19. A nose-drop package comprising a TB vaccine composition comprising an adjuvant comprising one or more substances selected from the group consisting of: a) monoglyceride preparations having at least 80% monoglyceride content and having the general formula:

```
CH₂—CH—CH₂
 |   |   |
 O   O   O
 |   |   |
 R   R   R
``` wherein R is H or an acyl group containing from 6 to 24 carbon atoms with the proviso proviso that two of the R groups are H, and b) a fatty acid with 6 to 24 carbon atoms; and as immunizing component, inactivated *Mycobacterium tuberculosis* bacteria.

20. The nose-drop package, according claims 19, wherein the *M. tuberculosis* bacteria are heat or formalin killed.

21. The nose-drop package according to claim 19, wherein the adjuvant has a content of monoglyceride in the monoglyceride preparation of at least 90% and the acyl chains of the monoglyceride in the monoglyceride preparation contains 8 to 20 carbon atoms.

22. The nose-drop package according to claim 19, wherein the adjuvant has a content of monoglyceride in the monoglyceride preparation of at least 95% and the acyl chains of the monoglyceride in the monoglyceride preparation contains 14 to 20 carbon atoms.

23. The nose-drop package according to claim 19, which further comprises pharmaceutical excipients selected from the group consisting of biocompatible oils, physiological saline solutions, preservatives, osmotic pressure controlling agents, carrier gases, pH-controlling agents, organic solvents, hydrophobic agents, enzyme inhibitors, water absorbing polymers, surfactants, absorption promoters and anti-oxidative agents.

24. The nose-drop package according to claim 19, wherein the monoglyceride preparation is mono-olein and the fatty acid is oleic acid, and the immunizing component is heat-killed *M. tuberculosis* bacteria.

25. The nose-drop package according to claim 19, wherein the composition is formulated into a preparation for mucosal administration.

26. The nose-drop package according to claim 25, wherein the mucosal administration is nasal, pulmonary, oral or vaginal administration.

27. The nose-drop package according to claim 24, wherein the adjuvant further comprises soybean oil.

28. A method of vaccinating a mammal against Tuberculosis (TB) which comprises mucosal administration to the mammal of a protection-inducing amount of a TB vaccine composition comprising an adjuvant comprising one or more substances selected from the group consisting of: a) monoglyceride preparations having at least 80% monoglyceride content and having the general formula:

```
CH₂—CH—CH₂
 |   |   |
 O   O   O
 |   |   |
 R   R   R
``` wherein R is H or an acyl group containing from 6 to 24 carbon atoms with the proviso that two of the R groups are H; and b) a fatty acid with 6 to 24 carbon atoms; and as immunizing component, inactivated *Mycobacterium tuberculosis* bacteria.

29. The method of vaccinating a mammal against Tuberculosis (TB) according to claim 28, wherein the *M. tuberculosis* bacteria are heat or formalin killed.

30. The method of vaccinating a mammal against Tuberculosis (TB) according to claim 28, wherein the adjuvant has a content of monoglyceride in the monoglyceride preparation of at least 90% and the acyl chains of the monoglyceride in the monoglyceride preparation contains 8 to 20 carbon atoms.

31. The method of vaccinating a mammal against Tuberculosis (TB) according to claim 28, wherein the adjuvant has a content of monoglyceride in the monoglyceride preparation of at least 95% and the acyl chains of the monoglyceride in the monoglyceride preparation contains 14 to 20 carbon atoms.

32. The method of vaccinating a mammal against Tuberculosis (TB) according to claim 28, which further comprises pharmaceutical excipients selected from the group consisting of biocompatible oils, physiological saline solutions, preservatives, osmotic pressure pH-controlling agents, carrier gases, PHcontrolling agents, organic solvents, hydrophobic agents, enzyme inhibitors, water absorbing polymers, surfactants, absorption promoters and anti-oxidative agents.

33. The method of vaccinating a mammal against Tuberculosis (TB) according to claim 28, wherein the monoglyceride preparation is mono-olein and the fatty acid is oleic acid, and the immunizing component is heat-killed *M. tuberculosis* bacteria.

34. The method of vaccinating a mammal against Tuberculosis (TB) according to claim 28, wherein the composition is formulated into a preparation for mucosal administration.

35. The method of vaccinating a mammal against Tuberculosis (TB) according to claim 34, wherein the mucosal administration is nasal, pulmonary, oral or vaginal administration.

36. The method of vaccinating a mammal against Tuberculosis (TB) according to claim 32, wherein the adjuvant further comprises soybean oil.

\* \* \* \* \*